United States Patent
Allen et al.

(10) Patent No.: US 11,033,756 B2
(45) Date of Patent: Jun. 15, 2021

(54) PORTAL IMAGING DURING RADIOTHERAPY

(71) Applicant: ELEKTA AB (PUBL), Stockholm (SE)

(72) Inventors: John Allen, West Sussex (GB); Colin Winfield, West Sussex (GB)

(73) Assignee: ELEKTA AB (FUEL), Stockholm (SE)

( * ) Notice: Subject to any disclaimer, the term of this patent is extended or adjusted under 35 U.S.C. 154(b) by 809 days.

(21) Appl. No.: 14/851,527

(22) Filed: Sep. 11, 2015

(65) Prior Publication Data

US 2016/0074673 A1    Mar. 17, 2016

(30) Foreign Application Priority Data

Sep. 11, 2014 (GB) ..................................... 1416055

(51) Int. Cl.
  *A61N 5/10*  (2006.01)
  *A61B 6/03*  (2006.01)

(52) U.S. Cl.
  CPC ........... *A61N 5/1049* (2013.01); *A61N 5/107* (2013.01); *A61N 5/1036* (2013.01);
  (Continued)

(58) Field of Classification Search
  CPC .......... A61N 2005/1054; A61N 5/1049; A61N 5/1047; A61N 5/1048; A61N 5/1081; A61N 5/1083
  See application file for complete search history.

(56) References Cited

U.S. PATENT DOCUMENTS

| | | | |
|---|---|---|---|
| 6,345,114 B1 * | 2/2002 | Mackie | A61N 5/1048 378/65 |
| 2003/0086526 A1 | 5/2003 | Clark et al. | |
| 2007/0195936 A1 | 8/2007 | Manthey et al. | |

FOREIGN PATENT DOCUMENTS

| | | |
|---|---|---|
| CN | 203694429 U | 7/2014 |
| EP | 1308185 A2 | 7/2003 |

(Continued)

OTHER PUBLICATIONS

UK Intellectual Property Office Search Report dated Mar. 3, 2015 (2 pages).

*Primary Examiner* — Christine H Matthews
(74) *Attorney, Agent, or Firm* — Finnegan, Henderson, Farabow, Garrett & Dunner LLP

(57) ABSTRACT

A radiotherapy apparatus comprises a source for producing a beam of ionising radiation along an axis, the beam covering a maximum aperture of the source, a collimator for collimating the beam to produce a collimated beam covering a sub-part of the maximum aperture, a patient support positioned in the path of the beam, a rotatable gantry, on which the source is mounted, for rotating the source around the patient support thereby to deliver the beam from a range of directions, an imaging device located opposite the source and with the patient support between the source and the imaging device, and mounted on the gantry via a drive member allowing translational motion of the imaging device in at least one direction perpendicular to the axis, and a control unit adapted to control the drive member to move the imaging device within the maximum aperture and maintain coincidence between the imaging device and the sub-part of the maximum aperture. Accordingly, the EPID can be moved during the treatment in order to maintain the collimated field of the radiation beam within the bounds of the EPID. This ensures that the image is valid and prevents damage to the EPID as a result of exposure of more sensitive (or less shielded) parts to the beam.

18 Claims, 5 Drawing Sheets

(52) U.S. Cl.
CPC ......... *A61N 5/1047* (2013.01); *A61N 5/1081*
(2013.01); *A61N 5/1083* (2013.01); *A61B*
*6/032* (2013.01); *A61N 2005/1054* (2013.01);
*A61N 2005/1074* (2013.01)

(56) References Cited

FOREIGN PATENT DOCUMENTS

| | | |
|---|---|---|
| JP | 2011189016 A | 9/2011 |
| WO | WO 2004/105574 A2 | 9/2004 |

* cited by examiner

PORTAL IMAGING DURING RADIOTHERAPY

CROSS-REFERENCE TO RELATED PATENT APPLICATIONS

This application claims priority from United Kingdom Patent Application No. 1416055.0, filed on Sep. 11, 2014, which is incorporated herein by reference in its entirety.

FIELD OF THE INVENTION

The present invention seeks to improve upon existing methods of portal imaging during radiotherapy treatment.

BACKGROUND ART

Radiotherapy is the treatment of lesions such as tumours with ionising radiation such as high-energy x-rays. The radiation interferes with cellular processes within the tumour and can lead to cellular death. To spare healthy tissue (such as skin or organs adjacent to the tumour, or through which the radiation needs to pass in order to treat the tumour), shaped radiation beams are aimed from several different angles to intersect at the tumour, thus delivering a peak dose in the tumour region and a lower dose elsewhere.

To allow delivery of the radiation from several angles, the radiation source is usually mounted on the end of a cantilever arm projecting out from a rotatable gantry. The gantry has an axis of rotation that is horizontal, and the radiation source has a field of view whose central axis is perpendicular to and intersects with the axis of rotation. Thus, the point of intersection or "isocentre" remains within the field of view of the source at all times, and the direction of the radiation beam rotates around the isocentre.

To shape the radiation beam, collimators are provided. These usually include one or more multi-leaf collimators (MLCs), which collimate the radiation field into the required shape by moving each of a number of long, narrow side-by-side leaves so that the tips of the leaves define the intended shape. Prior to radiotherapy, a treatment plan will usually be calculated based on the parameters of the radiotherapy apparatus and the desired three-dimensional dose distribution, which consists of a series of dose segments each characterised by a beam direction, beam shape (i.e. specific collimator positions) and dosage.

Portal images are images of the therapeutic radiation taken after attenuation by the patient, usually by capturing the image in a plate that is located on the opposite side of the patient to the radiation source. Thus, the radiation passes through the patient and then reaches the portal imager. Although the contrast in a portal image is relatively poor due to the nature of the high-energy x-radiation that is used for radiotherapy, the image is still useful. It is possible to discern some features of the patient anatomy in order to determine correct positioning, the overall shape of the radiation field is visible and provides a check of collimator function and field shape & size, and the attenuation (i.e. the difference between the observed radiation intensity after the patient and the known radiation intensity emitted towards the patient) gives information as to the dose actually received by the patient. All of these can be compared to that which was expected during the treatment planning stage.

Portal images were originally captured using port films, i.e. photographic plates. These films would serve as a record of the field shape, and if anatomy could be seen in the field then it could be also used to verify the position of the beam relative to the patient's anatomy. Electronic Portal Imaging Devices ("EPIDs") have now been in use for some time in preference to port films, as they have better sensitivity than films and allow the images to be collected and stored electronically. An EPID is now a well-established part of radiotherapy delivery.

Because EPIDs are now quite common on modern radiotherapy equipment, a number of uses for EPIDs have been developed that go beyond the original port-film single exposure use. This includes portal dosimetry (noted above) which attempts to recalculate the patient dose by a method such as back projection, in order to check the end to end QA process. Another example is the capturing of video images showing the dynamic movement of the MLC leaves. All these uses are possible with existing EPID hardware.

However, these new uses do have a limitation in that the field size of current EPIDs is smaller than the field sizes of most MLCs. For example, a typical MLC has a 40×40 cm field size when referenced to the isocentre, whereas a typical state-of-the-art EPID has a panel giving an effective image size of 26×26 cm at isocentre, and some EPIDs are smaller still (all dimensions being referenced to the isocentre). This is rarely a problem in obtaining an image of the treatment, however, because large field sizes are uncommon and so will usually fall onto the panel within its limits. Where the desired image is of an offset field, the panel can be manually adjusted to provide a corresponding offset.

US2007/0195936A1 discloses an arrangement in which the field size is checked to ensure that the EPID aperture will not be exceeded, and moves the MLC leaves as necessary in order to keep the beam shape within the confines of the EPID panel.

SUMMARY OF THE INVENTION

The present invention therefore provides a radiotherapy apparatus, comprising a source for producing a beam of ionising radiation along an axis, the beam covering a maximum aperture of the source, a collimator for collimating the beam to produce a collimated beam covering a sub-part of the maximum aperture, a patient support positioned in the path of the beam, a rotatable gantry, on which the source is mounted, for rotating the source around the patient support thereby to deliver the beam from a range of directions, an imaging device located opposite the source and with the patient support between the source and the imaging device, and mounted on the gantry via a drive member allowing translational motion of the imaging device in at least one direction perpendicular to the axis, and a control unit adapted to control the drive member to move the imaging device within the maximum aperture and maintain coincidence between the imaging device and the sub-part of the maximum aperture.

Accordingly, the EPID can be moved during the treatment in order to maintain the collimated field of the radiation beam within the bounds of the EPID. This ensures that the image is valid and prevents damage to the EPID as a result of exposure of more sensitive (or less shielded) parts to the beam. No restrictions need be placed on the positioning of the patient, meaning that she or he can be positioned as desired. The treatment can be unaffected, unlike the suggestion made in US2007/0195936A1.

There are various ways that the movement of the EPID can be controlled. One option is for the control unit to receive a treatment plan containing instructions for at least movement of the rotatable gantry, movement of the collimator, activation of the source, and movement of the drive member. In other words, alongside calculations of the necessary beam shapes and intensities over time, a treatment planning computer can also model the beam shape and position through the treatment (once the treatment is decided) and establish the EPID movements that will be needed in order to allow for that.

An alternative is to adjust the EPID position in real time during treatment. The control unit will then receive an output image from the imaging device and adjust the position of the imaging device in reliance on that image. Thus, for example, if a distance in the output image between an image of the collimated beam and an edge of the output image is less than a threshold, the control unit will instruct a movement of the drive member.

The gantry can be a rotatable drum, in which case the source can be attached to the gantry via an arm extending transversely to the drum, preferably with the beam axis co-incident with a rotation axis of the gantry.

Alternatively, the gantry can comprise a circular path around which the source and the imaging device can travel, the axis of the source being directed to the centre of the circular path.

In essence, therefore, the radiotherapy apparatus comprises a source arranged to emit a beam of therapeutic radiation and an imaging device for the therapeutic radiation, the source being movable to direct the beam towards a location from a plurality of directions and the imaging device being movable relative to the source, and a control unit arranged to co-ordinate the movement of both to ensure that the imaging device remains in the beam, as the source moves to different treatment positions.

BRIEF DESCRIPTION OF THE DRAWINGS

An embodiment of the present invention will now be described by way of example, with reference to the accompanying figures in which.

DETAILED DESCRIPTION OF THE EMBODIMENTS

As noted above, the field size of current EPIDs is smaller than the maximum apertures of most MLCs, although larger than most actual dose shapes. We have realised that this limitation becomes a problem when the EPID is used for portal dosimetry or to capture a dynamic MLC video under certain treatment conditions. As an example, we propose to discuss a volumetric modulated arc therapy (VMAT) delivery to an off-axis target such as a tumour present in one breast or lung. This is not the only example, however, and the invention is applicable in other contexts.

Figure 1:
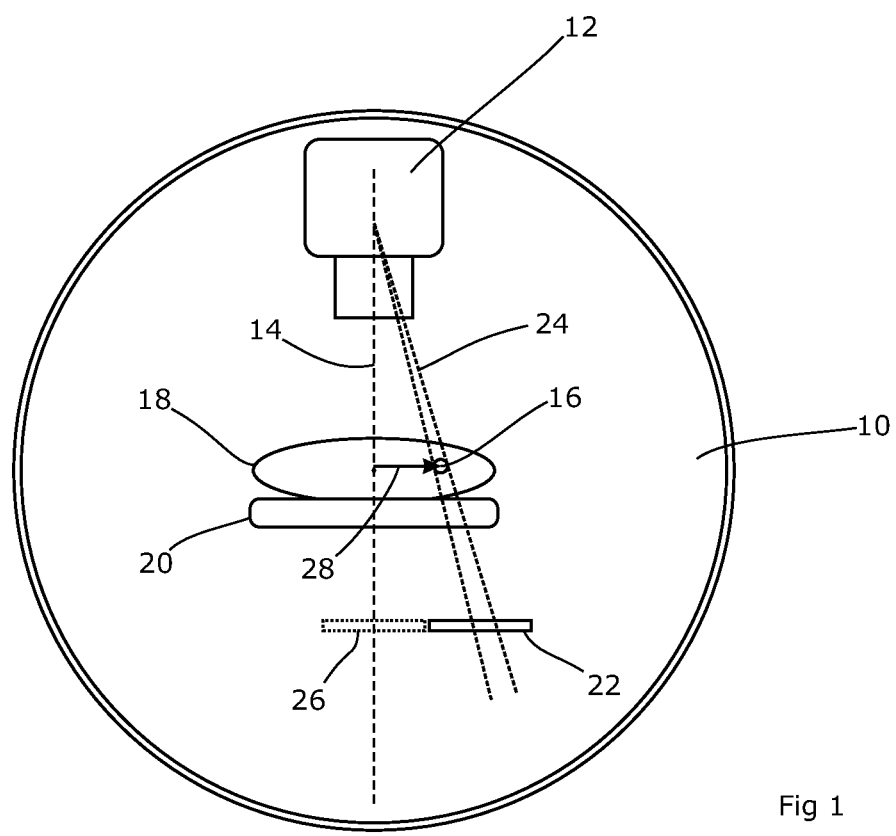
FIGS. 1 and 2 show a conventional radiotherapy apparatus in different rotational states.

FIG. 1 shows such a situation. A rotatable gantry 10 is set in an upright orientation, perhaps recessed into a wall or projecting through a false wall. It is in the form of a drum, rotatable around a horizontal axis; FIG. 1 is a view along that axis. The gantry 10 carries a radiation source 12 which can emit a collimated beam of therapeutic ionising radiation around a central axis 14, which intersects with the horizontal axis around which the gantry 10 rotates. As the gantry 10 rotates and carries the source 12 around, the central axis 14 of the beam sweeps out a vertical plane and approaches the point of intersection (often referred to as the isocentre) from all possible directions. This forms the basis of a radiotherapy treatment; by placing the tumour or other lesion at the isocentre and irradiating the tumour from a range of directions, a dose can be delivered to the tumour which is substantially greater than the dose delivered to tissue around the tumour.

The tumour 16 is positioned relative to the beam by placing the patient 18 on a patient support 20. This is separate to the gantry, usually supported on a floor in front of the gantry. Many modern patient supports offer adjustment in six axes, i.e. three translational axes and three rotational axes. In this way, after the patient 18 has been helped onto the support, their position can be adjusted via the patient support 20 so as to locate the tumour as desired. Some limits will of course be imposed by the range of motion of the patient support 20.

An EPID 22 is also carried by the gantry 10, located diametrically opposite the radiation source 12 to as to capture an image from the radiation beam after attenuation by the patient 18, as described above. As the gantry rotates, this will rotate with the gantry so as to maintain its position relative to the radiation source 12. The EPID could alternatively be carried by a separate structure, arranged to support the EPID in a suitable location opposite the source, but mounting it on the same gantry is likely to be easier and more accurate.

FIG. 1 illustrates a situation as outlined above, in which the tumour 16 is significantly off-centre within the patient 18. With the patient on the patient support 20, the tumour is then away from the central axis 14. The beam can however be collimated to compensate for this, thus producing an off-axis beam 24 which will deliver radiation to the tumour 16. This off-axis beam 24 will miss the EPID 22 if in its usual or default position 26 (shown in dotted lines), so the EPID 22 is manually adjusted into a suitable position as shown.

Figure 2:
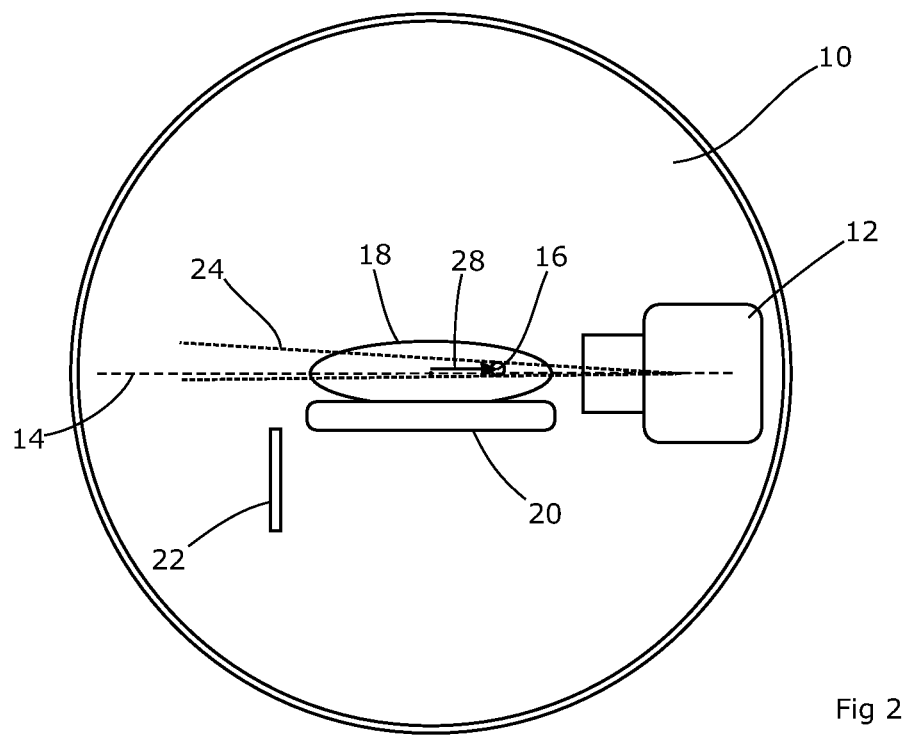

However, as the gantry rotates (FIG. 2) and the patient 18 remains stationary on the patient support 20, the degree of offset of the tumour 16 from the central axis 14 will vary. Considered geometrically, there will be a vector 28 from the isocentre to the tumour, and when the central axis 14 is perpendicular to the vector 28 (as in FIG. 1) then the offset as viewed along the central axis will be at is maximum. Equally, after a 90° rotation(as in FIG. 2), the central axis 14 will be parallel to the vector 28 and the offset will be at a minimum, possibly zero. This means that the EPID 22 in its offset position will no longer capture an image of the beam 24, as shown in FIG. 2. In addition, at some point in the rotation between the states shown in FIGS. 1 and 2, the beam 14 will leave the active imaging region and strike the edge of the EPID 22; this may damage neighbouring electronic components which are often much more radiation sensitive than the imaging panel itself, and are not intended to be exposed to the therapeutic beam.

Thus, although the actual field size (projected to isocentre) is likely to be smaller than the 26×26 cm aperture of the EPID 22, the offset position of beam may track across the full 40×40 cm beam aperture of the collimator as the gantry rotates. Thus, if the EPID is being used to collect portal dosimetry data, then some data will be lost and this will compromise the ability to accurately calculate the portal dose, as well as potentially causing damage to the EPID.

Figure 3:
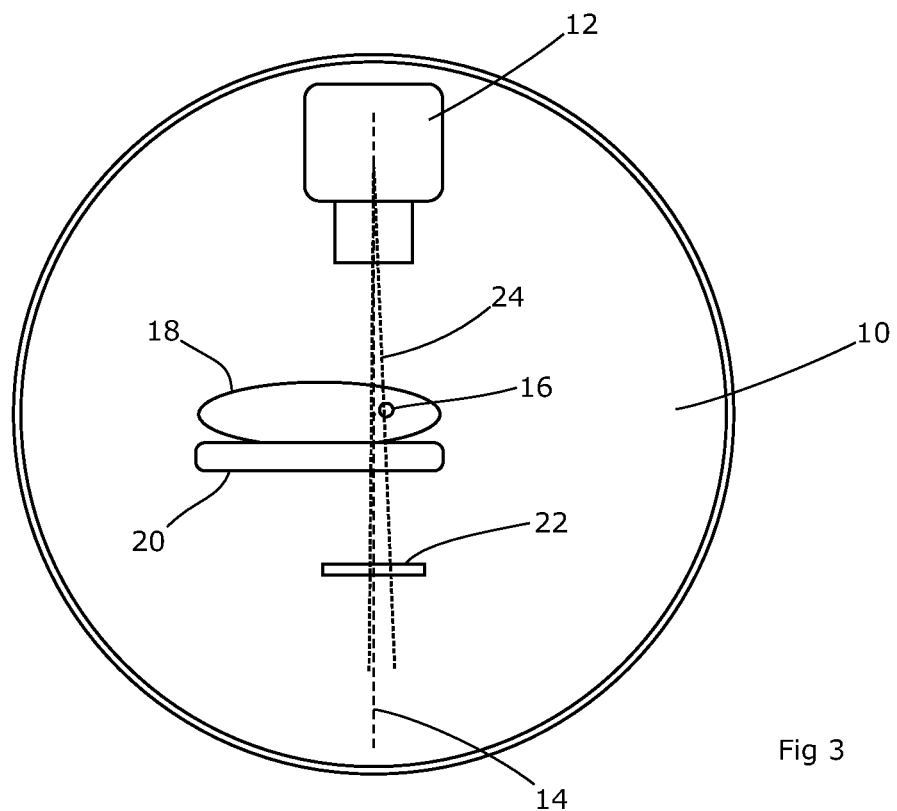
FIGS. 3 and 4 show the radiotherapy apparatus of FIGS. 1 and 2 in an alternative configuration.
Figure 4:
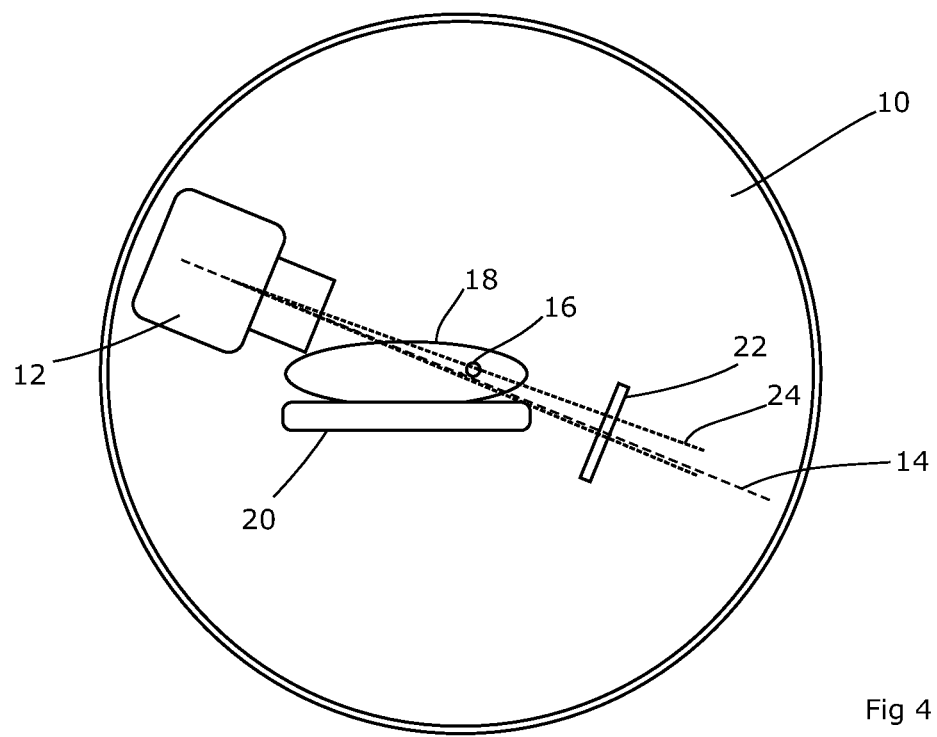

FIGS. 3 and 4 show the alternative, to position the patient off-axis via adjustment of the patient support 20 (or otherwise). Thus, the tumour is placed at or nearer the isocentre. As shown in FIG. 3, this means that distance between the isocentre and the tumour 16 is small, and the EPID 22 does not need to be offset. As shown in FIG. 4, rotation of the gantry 10 leaves the beam 24 still within the effective aperture of the EPID 22. However, this raises a risk of collision between the radiation head 12 rotating around the patient support 20 and the off-axis patient support 20. Any further rotation in an anti-clockwise direction beyond that shown in FIG. 4 will lead to a collision and possible injury to the patient, as well as damage to the apparatus. As a result, such treatment may have to be planned around a limited range of rotational movement of the head in order to prevent collision. This is possible within the bounds of treatment planning, but may lead to a sub-optimal treatment plan. Alternatively, the treatment can be interrupted in order to reposition the patient and/or imaging panel, but this will prolong the duration of the treatment session, which is undesirable for the patient and hospital.

So, the treatment can be planned with the tumour placed away from the isocentre on the machine, to allow the patient to be positioned centrally, avoid collision risk, and allow use of the full 360° rotation of the source, but the EPID will not be available. Alternatively, the tumour can be positioned centrally, but the full range of rotation may not be available, so the treatment may be sub-optimal. In a further alternative, according to US2007/0195936A1, the MLC leaf positions are adjusted to ensure that the EPID is protected and usable, but this will also affect the treatment and render it sub-optimal.

Figure 5:
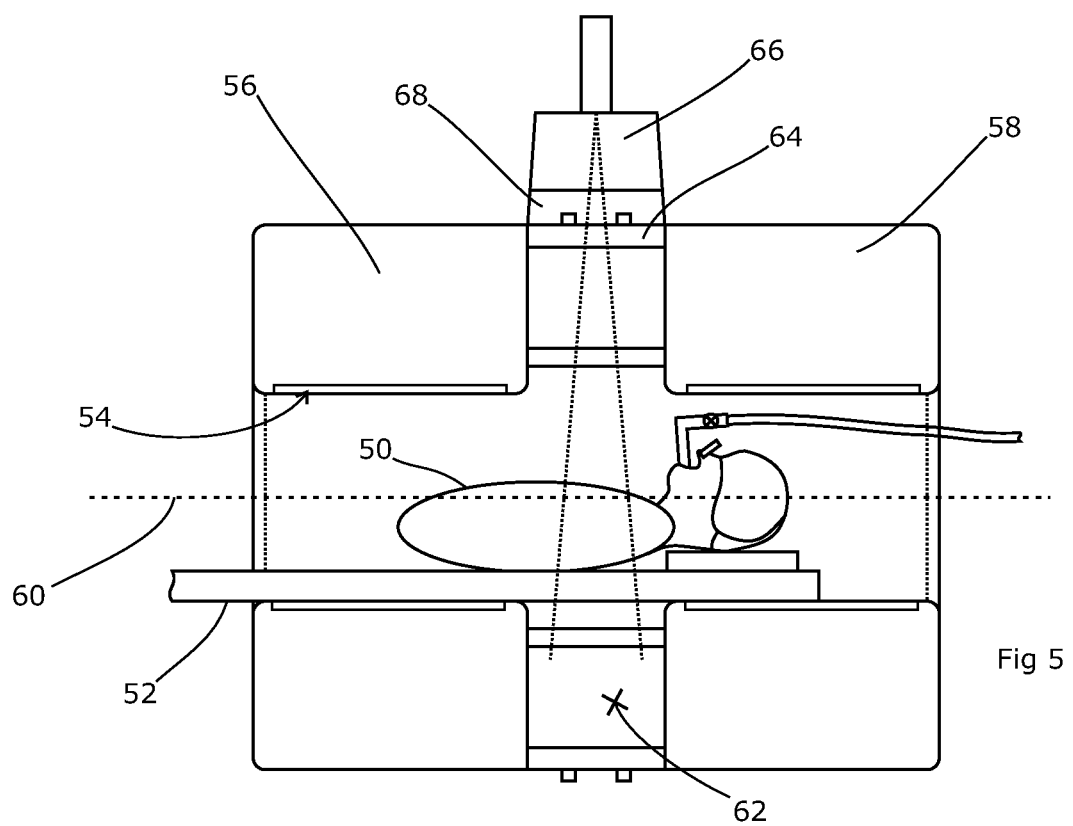
FIGS. 5 and 6 show an alternative radiotherapy apparatus.
Figure 6:
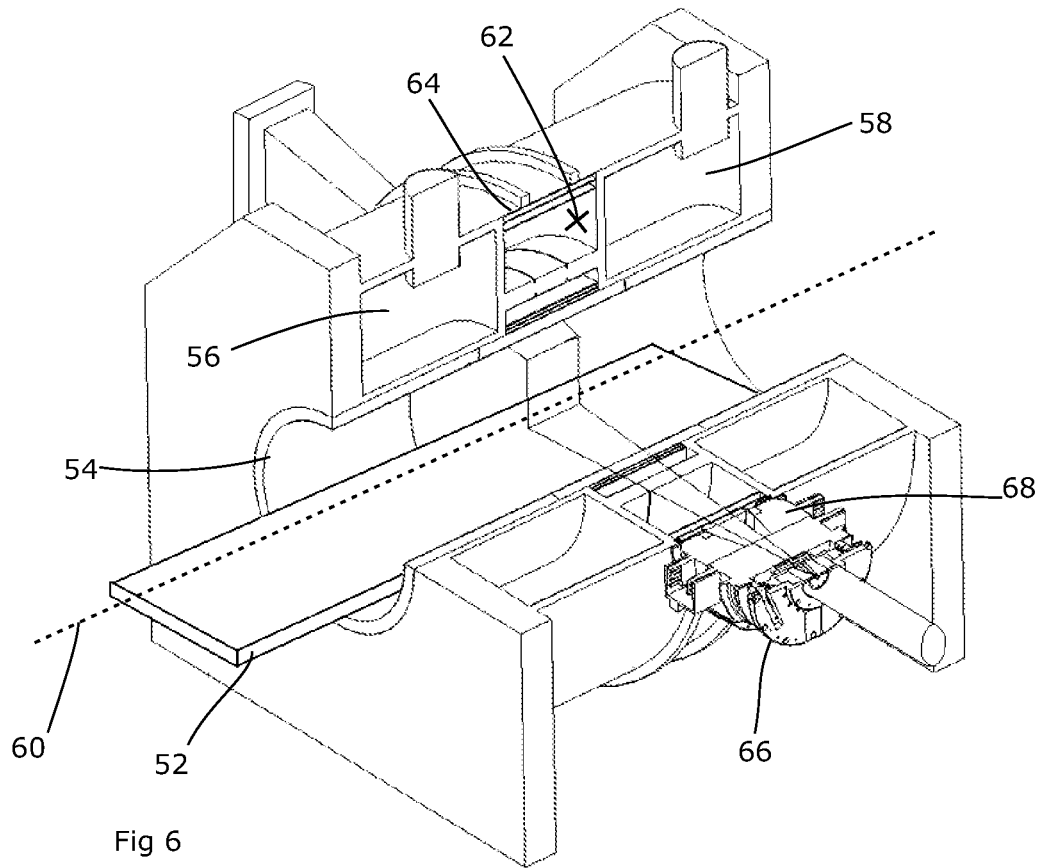

FIGS. 5 and 6 illustrate a further type of radiotherapy apparatus. Efforts are currently being made to integrate MRI scanning with radiotherapy; at present CT scanning (usually cone-beam CT) is easily integrated simply by adding a lower-energy diagnostic source to the gantry together with an opposing detector, usually located 90° away from the therapeutic beam and the EPID. The integration of MRI scanning is more complex as a design needs to be found that allows for the substantial magnets required by MRI systems, although once this is done there are benefits in that the background dose of ionising radiation given to the patient is reduced as compared to a CT scan. FIGS. 5 and 6 show such a system; the patient 50 (not shown in FIG. 6) lies on a patient support 52 that can be translated longitudinally into and out of a bore 54. A pair of primary magnet windings 56, 58 are arranged concentrically around the bore 54, spaced longitudinally along the horizontal axis 60 of the bore 54 so that each winding extends from a respective end of the bore 54 towards the centre of the bore. A gap 62 is left at that centre of the bore between the two windings, and a rotating gantry 64 fits within that gap 62 and is able to rotate around the bore 54. A therapeutic source 66 is mounted on the gantry 64 and is therefore rotateable around the bore 54 together with the gantry 64; collimators 68 are provided within the source 66 so that a radiotherapeutic dose can be delivered to the patient 50 in an otherwise known manner. An EPID (not shown) is mounted on the gantry 64, opposite the source 66 and is used in a manner corresponding to that of the apparatus of FIGS. 1 to 4.

An apparatus of this type presents additional difficulties, in that where the target is offset it will not generally be possible to offset the patient as shown in FIGS. 3 and 4, as the patient must be located within the defined bore 54 and cannot be displaced significantly. Therefore, the only option is to offset the beam by use of the collimator 68, leading to the difficulties illustrated in relation to FIGS. 1 and 2.

Figure 7:
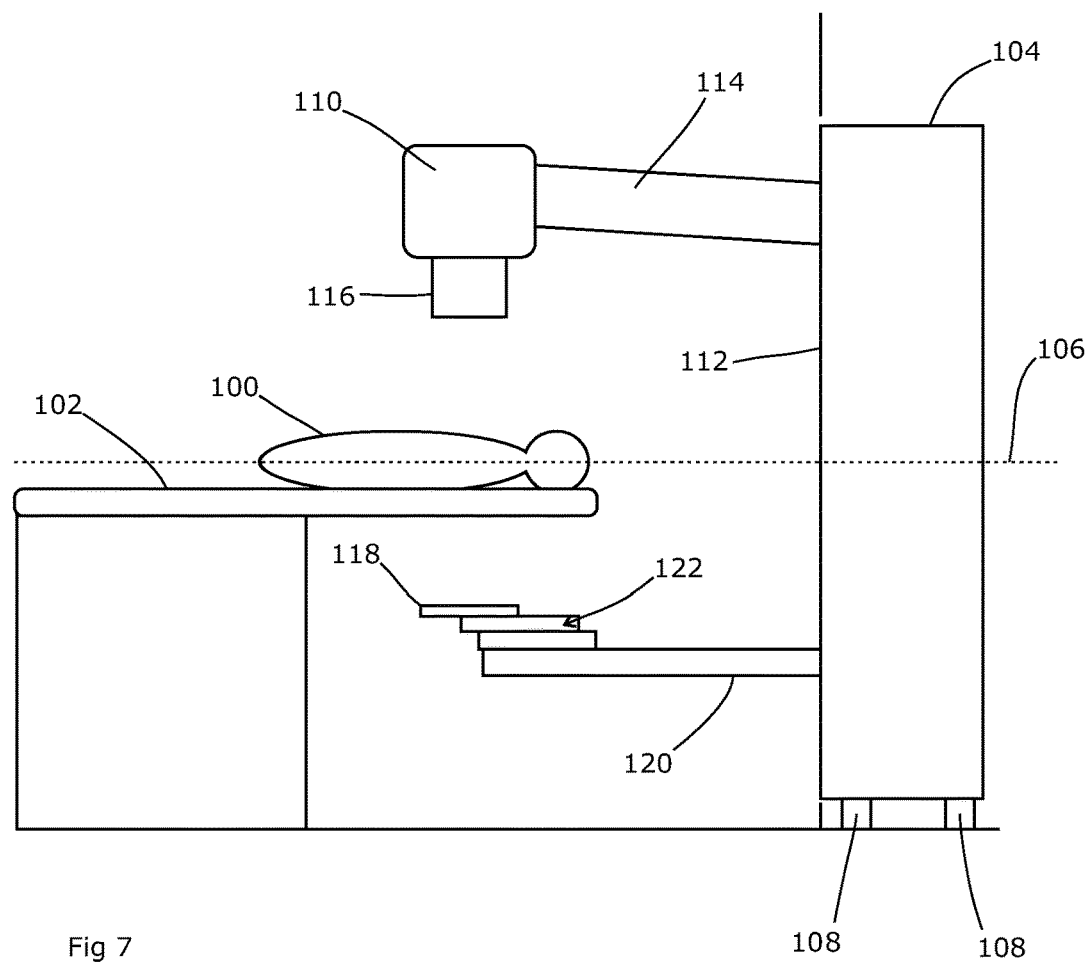
FIG. 7 shows a radiotherapy apparatus according to the present invention.
Figure 8:
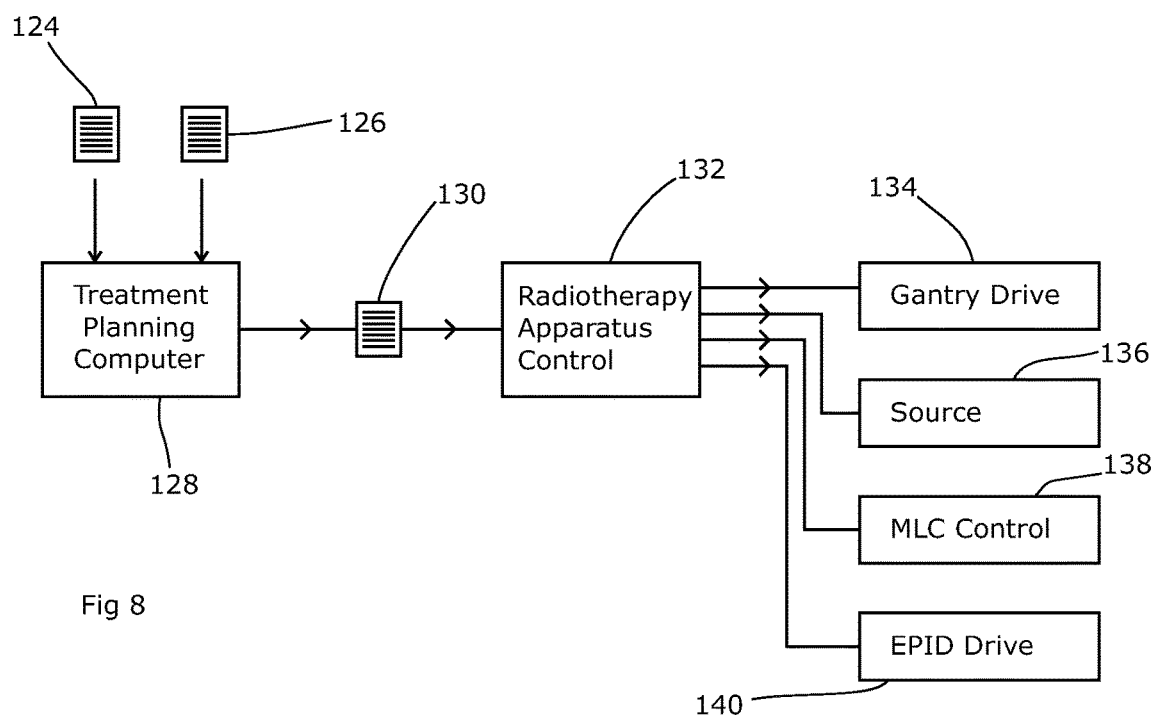
FIG. 8 shows a control schema for the radiotherapy apparatus of FIG. 7.

Both problems can be addressed using the apparatus of FIG. 7 in conjunction with the control schema of FIG. 8. FIG. 7 shows a radiotherapy apparatus of the same general type as FIGS. 1 to 4, although the invention is also applicable to apparatus of the type shown in FIGS. 5 and 6 by making a corresponding change. Thus, a patient 100 is supported on a patient support 102 in front of a gantry 104 that is rotatable around a horizontal axis 106. In practice, the gantry 104 is in the form of a cylindrical drum resting on its circular face on a number of supporting wheels 108, and driven to rotate by a motor (not shown) that engages with an edge of the drum. The drum thus rotates around its centre, through which the axis 106 passes.

A radiotherapeutic source 110 is mounted on the drum, offset from its front face 112 by a gantry arm 114. The source 110 is aimed towards the rotation axis 106, thus defining an isocentre where the rotation axis 106 meets the central axis of the beam emitted by the source 110. A collimator arrangement 116 is included in the radiation source 110 so as to shape the beam as desired and allow the required dose distribution to be built up.

An EPID 118 is also mounted on the gantry 104, via a gantry arm 120 that extends transversely from the front face 112 of the gantry 104 so as to place the EPID 118 generally opposite the source 110, with the patient 100 and the patient support 102 between them. This allows the EPID 118 to capture an image of the beam as attenuated by the patient 100. The EPID 118 is connected to its gantry arm 120 via a series of servo-controlled linkages 122 that allow x-y movement of the EPID 118 relative to the gantry arm 120. The two translation axes of the linkages 122 are arranged transverse to the beam direction, so the effect of translating the EPID 118 is to scan it across the field of the beam. The gantry arm 120 and/or the linkages 122 may be also able to move the EPID 118 in a z-direction, i.e. towards or away from the source 110. However, for the purposes of the present invention we are principally concerned with movement in the x and y directions; motion in the z direction is in principle irrelevant to the invention apart from its influence on the effective image size within the beam aperture.

The movement of the EPID 118 in the y direction (i.e. parallel to the rotation axis 106) will usually be in a straight line. Its movement in the x direction (i.e. perpendicular to both the rotation axis 106 and the beam axis, into and out of the page in FIG. 7) is ideally along a circular path centred on the rotation axis 106, in order to maintain a fixed distance from the source 110. However, for ease of manufacture it is likely that movement in a straight line will be a good first approximation to circular movement, especially for smaller translational movements. It is likely that correction of the images to account for the difference between circular and linear movement will be straightforward.

FIG. 8 shows the control schema for the apparatus of FIG. 7. A physician prepares a prescription 124 setting out a dose and a dose distribution that are to be delivered to the patient. A separate document 126 sets out the delivery limitations imposed by the apparatus to be used, such as the resolution of the collimators, speed of collimator movement and gantry movement, the dose characteristics of the beam, etc. A treatment planning computer 128 processes the prescription and the machine characteristics according to known computational methods, to produce a treatment plan 130. This sets out a sequence of gantry movements, collimator movements, beam intensities etc. which the apparatus can then follow in order to create a dose distribution in the patient which corresponds to the prescription. This treatment plan 130 is then passed to the apparatus control unit 132. The control unit 132 is arranged to control the gantry drive motor 134, the radiation source 136, and the multi-leaf collimator ("MLC") drives 138. Thus, once initiated by a clinician, the apparatus control unit 132 can deliver the radiotherapy treatment.

In practice, the apparatus control unit 132 may comprise several sub-modules, each attending to different functional aspects of the apparatus, which may be distributed around the apparatus as required.

Also shown in FIG. 8 is a link from the apparatus control unit 132 to the servo drive motors 140 of the EPID linkages 122 (FIG. 7), thus allowing the apparatus control unit to control the x-y position of the EPID 118. This permits the apparatus control unit 132 to adjust the position of the EPID within the beam aperture so as to maintain the beam within the bounds of the EPID, thus obtaining an accurate image of the attenuated beam and also protecting the EPID from the beam. This control can be done in one of two ways.

A first way is to predict the necessary EPID movements and adjust it accordingly. Accordingly, the treatment planning computer 128 can use its a priori knowledge of the collimator positions during the treatment to calculate the required position of the EPID 118 at each point during the treatment. This can be done using simple ray projection methods, either to determine where the beam will fall in the plane containing the EPID, or to determine a correlation between EPID positions and MLC leaves and positions, from either of which the necessary EPID position for each collimator shape during the treatment can be determined. If a collimator shape is called for during treatment that is so large or unusual that the EPID cannot accommodate it, then the system can either issue a warning to the clinician or can incorporate the EPID size as an apparatus limitation within document 126 and then calculate or re-calculate the treatment plan, as necessary. The EPID positions during treatment that are determined in this way can then be incorporated into the treatment plan 130 and passed to the apparatus control unit 132. During the treatment, the apparatus control unit 132 can then control the EPID drive motors 140 as required in order to achieve this. Adjustments to the planned EPID positions may of course be needed in view of any adjustments made to the planned collimator positions, such as to compensate for movement of the target.

Of course, the EPID position calculations could be done by a separate module within the treatment planning computer 128, or by a different computing element, or by the apparatus control unit 132. In the latter case, the necessary EPID positions could be calculated in real time while acting on the collimator positions contained in the treatment plan.

Figure 9:
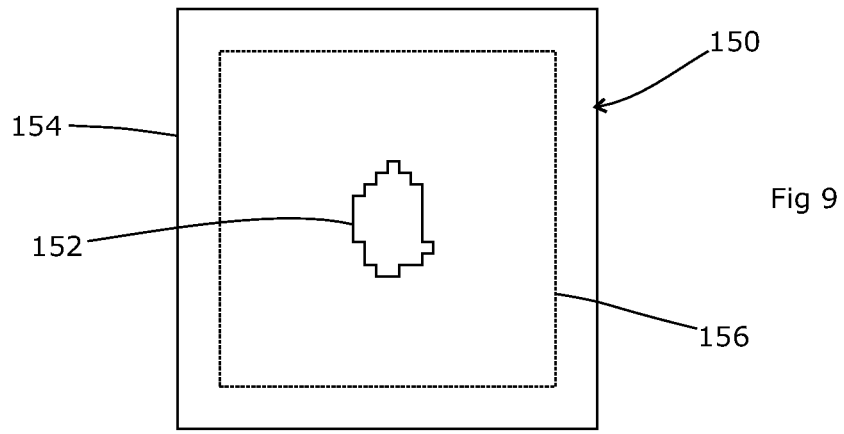
FIGS. 9 to 11 show portal images derived from the apparatus of FIG. 7.
Figure 10:
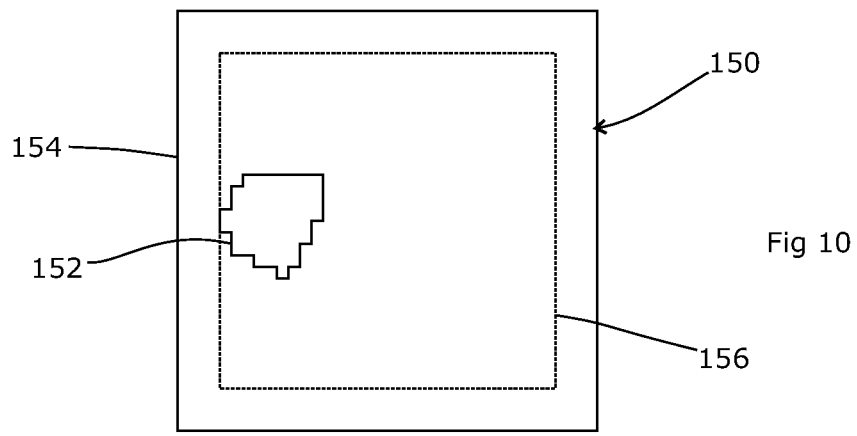
Figure 11:
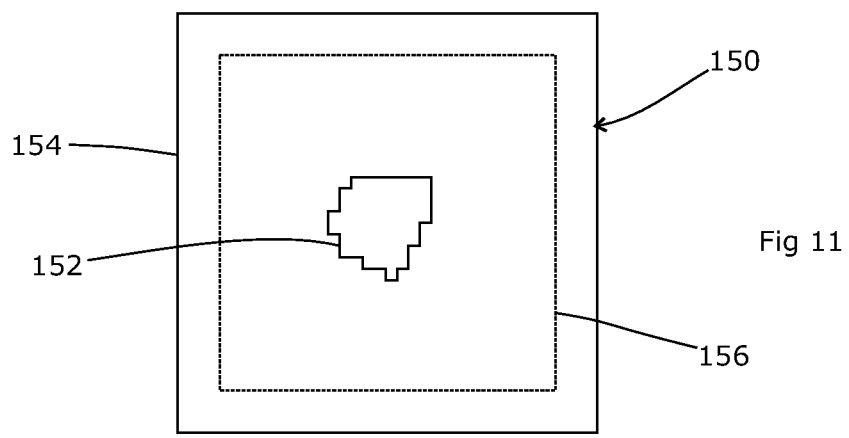

The alternative control mechanism for the EPID drive motors is a reactive feedback method which uses the images obtained from the EPID in order to determine a necessary movement. This is shown in FIGS. 9 to 11. FIG. 9 shows an image 150 obtained from the EPID; the predominant feature in the EPID is the shape 152 of the beam as shaped by the multi-leaf collimator. Outside this outline 152, the image is essentially dark other than any inevitable leakage; within this outline there will be information as to the attenuation by the patient, but for the purposes of clarity this detail is omitted from FIGS. 9 to 11. In FIG. 9, the beam shape 152 is in the centre of the EPID aperture 154 and so no action needs to be taken.

As the treatment progresses, with rotation of the gantry and adjustment of the collimator shape, the beam shape 152 may well move as shown in FIG. 10. The apparatus control unit 132 therefore monitors the image 150 to detect when the beam shape 152 reaches the edge of a pre-defined margin 156 around the edge of the image. FIG. 10 shows that the beam shape 152 has moved sufficient to touch the edge of the margin 156 at 158. The apparatus control unit 132 therefore instructs the servo drive motors 140 of the EPID linkages 122 to move the EPID in the appropriate direction(s) to bring the beam shape 152 back to the centre of the image as shown in FIG. 11. In this way, a negative feedback loop is created which serves to keep the beam shape 152 within the bounds of the image 150, responding both to gross movements of the beam shape (such as following rotation around an offset target) and to changes in the beam shape that take it towards an edge (such as due to reconfiguration of the collimator shape).

As illustrated in FIGS. 9 to 11, the margin 156 is quite narrow. In practice, the choice of margin size will be a balance between factors, to be assessed by the skilled person. A narrow margin will reduce the number of movements of the EPID, thus reducing wear on the EPID drive motors and (possibly) reducing the complexity of correcting the images for position, but will require faster movement of the EPID and less lag in initiating movement. Equally, a larger margin means that the EPID drive motors need not react as promptly or move as quickly, but raises the possibility of very large beam shapes causing problems if they approach the margin on two or more sides. One possibility is a variable margin, chosen according to how large the beam shape is, with smaller beam shapes implying a larger margin and large beam shapes prompting a relaxation of the margin size.

In either case, the EPID position is ideally recorded during the treatment, such as in conjunction with the images obtained from it. This then allows the images to be corrected for the EPID offset. Alternatively, the images could be processed in real time by offsetting them against (say) a plain background by an amount corresponding to the EPID offset when they were captured. The saved set of images are then in a comparable format for later analysis.

Accordingly, the present invention allows the EPID to be used for real-time diagnostic purposes, regardless of the type of treatment, and without having to make potentially detrimental adjustments to the treatment plan. It will of course be understood that many variations may be made to the above-described embodiment without departing from the scope of the present invention.

The invention claimed is:

1. A radiotherapy apparatus for treating a target portion of a patient, comprising:
   a source for producing a beam of ionizing radiation toward a rotation axis, the beam covering a maximum aperture of the source, the source having a central axis that is perpendicular to the rotation axis, wherein the central axis and the rotation axis intersect at an isocenter;
   a collimator for collimating the beam to produce a collimated beam directed along a beam axis extending toward a tumor within the target portion and covering a sub-part of the maximum aperture, wherein the beam axis is offset with respect to the isocenter, and wherein the tumor is located in a position in the offset with respect to the isocenter;
   a patient support positionable in the path of the beam;
   a rotatable gantry, on which the source is mounted, that rotates around the rotation axis and thereby to rotate the source around the patient support and thereby to deliver the beam from a range of rotational positions, wherein the tumor is located in the offset position for at least one rotational position;
an imaging device located opposite the source, such that the patient support is located between the source and the imaging device, and the imaging device is mounted on the rotatable gantry via a drive member adapted to allow translational motion of the imaging device in at least one direction perpendicular to the central axis; and
a control unit configured to provide instructions to:
control the drive member to move the imaging device during rotation of the source; and
maintain alignment between the tumor at the offset position with respect to the isocenter, the imaging device, and the collimated beam that covers the sub-part of the maximum aperture.

2. The radiotherapy apparatus according to claim 1, wherein the control unit receives a treatment plan containing instructions for:
rotation of the rotatable gantry according to the treatment plan;
movement of the collimator for producing the collimated beam according to the treatment plan;
activation of the source to produce a beam to be provided to the collimator; and
movement of the drive member according to the treatment plan.

3. The radiotherapy apparatus according to claim 1, wherein the control unit is configured to provide instructions adapted to:
analyze an output image from the imaging device;
determine if a distance in the output image between an image of the collimated beam and an edge of the output image is less than a threshold; and
instruct a movement of the drive member to maintain alignment between the tumor at the offset position with respect to the isocenter, the imaging device, and the collimated beam that covers the sub-part of the maximum aperture.

4. The radiotherapy apparatus according to claim 1, wherein the rotatable gantry is a rotatable drum.

5. The radiotherapy apparatus according to claim 4, wherein the source is attached to the rotatable gantry via an arm extending transversely to the rotatable drum.

6. The radiotherapy apparatus according to claim 1, wherein the rotatable gantry is adapted to rotate the source and the imaging device in a circular path, wherein the central axis is directed to a center of the circular path located on the rotation axis.

7. A radiotherapy apparatus for treating a target portion of a patient comprising:
a rotatable gantry rotating around a rotation axis;
a source having a central axis that is perpendicular to the rotation axis, the central axis and the rotation axis intersecting at an isocenter, the source being arranged to emit a beam of therapeutic radiation along a beam axis and toward the rotation axis, wherein the beam axis is offset with respect to the isocenter, and wherein the rotation of the gantry causes the source to rotate and to direct the beam along the beam axis towards a tumor within the target portion from a plurality of rotational positions, wherein the tumor is located in a position that is offset with respect to the isocenter and located in the offset position for at least one rotational position;
an imaging device for the therapeutic radiation, the imaging device being movable relative to the source; and
a control unit configured to provide instructions to coordinate the rotation of the source and the movement of the imaging device to ensure that the imaging device remains in the beam, as the source rotates to different rotational positions and directs the beam towards the tumor in the offset position with respect to the isocenter.

8. The radiotherapy apparatus according to claim 7, wherein the control unit receives a treatment plan containing instructions for:
rotation of the rotatable gantry according to the treatment plan;
movement of a collimator for producing a collimated beam according to the treatment plan;
activation of the source to produce the beam to be provided to the collimator; and
movement of a drive member according to the treatment plan.

9. The radiotherapy apparatus of claim 7, comprising a patient support positionable in the path of the beam.

10. The radiotherapy apparatus of claim 9, wherein the rotatable gantry has the source attached thereto, and the rotation of the gantry causes the source to rotate around the patient support to direct the beam from the plurality of rotational positions.

11. The radiotherapy apparatus of claim 10, wherein the rotatable gantry comprises a rotatable drum.

12. The radiotherapy apparatus of claim 11, wherein the source is attached to the rotatable gantry via an arm extending transversely to the rotatable drum.

13. A radiotherapy apparatus for treating a target portion of a patient, comprising:
a rotatable gantry rotating around a rotation axis;
a source for producing a beam of ionizing radiation along a beam axis, the source having a central axis that is perpendicular to the rotation axis, the central axis and the rotation axis intersecting at an isocenter, wherein the beam axis is offset with respect to the isocenter, and wherein the rotation of the gantry causes the source to rotate and to direct the beam along the beam axis towards a tumor within the target portion from a plurality of rotational positions, wherein the tumor is located in a position that is offset with respect to the isocenter and located in the offset position for at least one rotational position;
an imaging device located opposite the source, the imaging device being mounted on the rotatable gantry via a drive member adapted to allow translational motion of the imaging device in at least one direction perpendicular to the central axis; and
a control unit configured to provide instructions to control the drive member to move the imaging device to maintain the imaging device in the beam as the source rotates to different rotational positions and directs the beam towards the tumor in the offset position with respect to the isocenter.

14. The radiotherapy apparatus of claim 13, comprising a patient support positionable in the path of the beam.

15. The radiotherapy apparatus of claim 14, wherein the rotatable gantry has the source attached thereto, and the rotation of the gantry causes the source to rotate around the patient support to direct the beam from the plurality of rotational positions.

16. The radiotherapy apparatus of claim 15, wherein the rotatable gantry comprises a rotatable drum.

17. The radiotherapy apparatus of claim 16, wherein the source is attached to the rotatable gantry via an arm extending transversely to the rotatable drum.

18. The radiotherapy apparatus of claim 15, wherein the rotatable gantry is adapted to rotate the source and the imaging device in a circular path, wherein the central axis is directed to a center of the circular path located on the rotation axis.

* * * * *

UNITED STATES PATENT AND TRADEMARK OFFICE
CERTIFICATE OF CORRECTION

| | |
|---|---|
| PATENT NO. | : 11,033,756 B2 |
| APPLICATION NO. | : 14/851527 |
| DATED | : June 15, 2021 |
| INVENTOR(S) | : John Allen et al. |

Page 1 of 1

It is certified that error appears in the above-identified patent and that said Letters Patent is hereby corrected as shown below:

On the Title Page

Item (73), "Assignee: ELEKTA AB (FUEL), Stockholm (SE)" should read --Assignee: ELEKTA AB (PUBL), Stockholm (SE)--.

Item (30), under "Foreign Application Priority Data," "1416055" should read --1416055.0--.

Item (74), "*Attorney, Agent or Firm* – Finnegan, Henderson, Parabow, Garrett & Dunner LLP" should read --*Attorney, Agent or Firm* – Finnegan, Henderson, Farabow, Garrett & Dunner LLP--.

Signed and Sealed this
Second Day of August, 2022

Katherine Kelly Vidal
*Director of the United States Patent and Trademark Office*